United States Patent
Dubremetz et al.

(10) Patent No.: US 7,964,185 B2
(45) Date of Patent: Jun. 21, 2011

(54) APICOMPLEX VACCINE STRAINS OF A FAMILY OF SARCOCYSTIDAE

(75) Inventors: Jean-François Dubremetz, Montpellier (FR); Daniel Bout, Cerelles (FR); Maryse Lebrun, Jacou (FR); Martine Soête, Arras (FR); Odile Cerede, Fondettes (FR)

(73) Assignees: Institut National de la Recherche Agronomique, Paris (FR); Centre National de la Recherche Scientifique, Paris (FR); Universite Francois Rabelais, Tours Cedex (FR)

( * ) Notice: Subject to any disclaimer, the term of this patent is extended or adjusted under 35 U.S.C. 154(b) by 159 days.

(21) Appl. No.: 10/585,721

(22) PCT Filed: Jan. 13, 2005

(86) PCT No.: PCT/FR2005/000074
§ 371 (c)(1),
(2), (4) Date: Aug. 8, 2008

(87) PCT Pub. No.: WO2005/072754
PCT Pub. Date: Aug. 11, 2005

(65) Prior Publication Data
US 2009/0053266 A1    Feb. 26, 2009

(30) Foreign Application Priority Data
Jan. 13, 2004  (FR) .................. 04 00260

(51) Int. Cl.
*A01N 63/00* (2006.01)
*A61K 39/012* (2006.01)
*A61K 48/00* (2006.01)
(52) U.S. Cl. .................. 424/93.2; 424/273.1
(58) Field of Classification Search .......... None
See application file for complete search history.

(56) References Cited

U.S. PATENT DOCUMENTS
6,248,329 B1 * 6/2001 Chandrashekar et al. . 424/191.1

FOREIGN PATENT DOCUMENTS
FR    2 8050466 A    8/2001

OTHER PUBLICATIONS

Bassuny et al 2003 Infection and Immunity vol. 71 No. 11 pp. 6222-6228.*
Meissner et al 2002 Journal of Cell Science 115 pp. 563-574.*
Ellis Chapter 29 of Vaccines, Plotkin, et al. (eds) WB Saunders, Philadelphia, 1998, especially p. 571, paragraph 2).*
Buxton, D., et al.: "A Commercial Vaccine of Ovine Toxoplasmosis", Parasitology, Cambridge University Press, London, GB, vol. 110, 1995, pp. S11-S16.
Chartier, C., et al.: "Efficacite Vaccinale de la Souche S48 de Toxoplasama Gondii Vis-à-vis D'Une Infection Experimentale Chez La Chevre", Annales de Medicine Veterinaire, Faculte de Medecine Veterinaire, Liege, BE, vol. 145, No. 3, 200.1, pp. 202-209.
Montoya, J. G., et al.: Toxoplasmosis, Lancet The, Lancet Limited, London, GB, vol. 363. No. 9425, Jun. 12, 2004, pp. 1965-1976.
Fourmaux, M. N., et al.: "The MIC1 Microneme Protein of Toxoplasma Gondii Contains a Duplicated Receptor-Like Domain and Binds to Host Cell Surface", Molecular and Biochemical Parasitology Elsevier Science Publishers, Amsterdam, NL, vol. 83, 1996, pp. 201-210.
Bourguin, I., et al.: "Murine Dendtritic Cells Pulsed In Vitro With Toxoplasma Gondii Antigens Induce Protective Immunity In Vivo", Infection and Immunity, American Society for Microbiology, Washington, US, vol. 66, No. 10, Oct. 1998, pp. 4867-4874.
Dubremetz, J. F.: "Host Celll Invasion by Toxoplasma Gondii", Trends in Microbiology, Elsevier Science Ltd., Kidlington, GB, vol. 6, No. 1, Jan. 1998, pp. 37-40.
Bhopale, G., et al.: "Development of a Vaccine for Toxoplasmosis: Current Status", Microbes and Infection, vol. 5, 2003, pp. 457-462.

* cited by examiner

*Primary Examiner* — Robert A Zeman
*Assistant Examiner* — Nina A Archie
(74) *Attorney, Agent, or Firm* — Morgan, Lewis & Bockius LLP

(57) ABSTRACT

The invention relates to attenuate mutated strains of apicomplex of a family of Sarcocystidae, containing inactivated MIC1 and MIC3 adhesins and to the use thereof for a vaccine.

2 Claims, 6 Drawing Sheets

SEQUENCE LISTING

```
<160> NUMBER OF SEQ ID NOS: 6

<210> SEQ ID NO 1
<211> LENGTH: 27
<212> TYPE: DNA
<213> ORGANISM: Artificial
<220> FEATURE:
<223> OTHER INFORMATION: Synthetic primer

<400> SEQUENCE: 1
gtgtaagctt cagcgagtct ctgagag                                        27

<210> SEQ ID NO 2
<211> LENGTH: 32
<212> TYPE: DNA
<213> ORGANISM: Artificial
<220> FEATURE:
```

```
<223> OTHER INFORMATION: Synthetic primer

<400> SEQUENCE: 2
ggggtaccga gctcatgagc agaagctgcc ag                                32

<210> SEQ ID NO 3
<211> LENGTH: 32
<212> TYPE: DNA
<213> ORGANISM: Artificial
<220> FEATURE:
<223> OTHER INFORMATION: Synthetic primer

<400> SEQUENCE: 3
ctgaattcag atcttaccag tgttggacaa gg                                32

<210> SEQ ID NO 4
<211> LENGTH: 31
<212> TYPE: DNA
<213> ORGANISM: Artificial
<220> FEATURE:
<223> OTHER INFORMATION: Synthetic primer

<400> SEQUENCE: 4
ggggtacccc ttgctaggta accactcgtg c                                 31

<210> SEQ ID NO 5
<211> LENGTH: 36
<212> TYPE: DNA
<213> ORGANISM: Artificial
<220> FEATURE:
<223> OTHER INFORMATION: Synthetic primer

<400> SEQUENCE: 5
gcacaattga gatctaaaat gcgaggcggg acgtcc                            36

<210> SEQ ID NO 6
<211> LENGTH: 41
<212> TYPE: DNA
<213> ORGANISM: Artificial
<220> FEATURE:
<223> OTHER INFORMATION: Synthetic primer

<400> SEQUENCE: 6
tgctatgcat tcctaggctg cttaattttc tcacacgtca c                      41
```

APICOMPLEX VACCINE STRAINS OF A FAMILY OF SARCOCYSTIDAE

Figure 1:
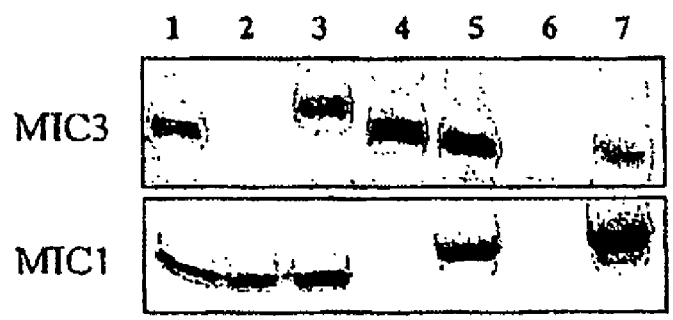

The present invention relates to attenuated mutant strains of Apicomplexa of the family Sarcocystidae, such as *Toxoplasma* and *Neospora*, and to the uses thereof for vaccines.

The Apicomplex phylum (branch Apicomplexa) groups together a large number of predominantly intracellular parasites. These parasites are responsible for diseases such as toxoplasmosis, malaria, neosporosis, coccidiosis and cryptosporidiosis. They have in common a specific process of host cell invasion in several steps, resulting in the formation of a parasitophorus vacuole in which the parasite develops (Menard et al., Cell Microbiol. 3: 63-73, 2001; Soldati et al., Int. J. Parasitol. 31: 1293-1302, 2001).

*Toxoplasma gondii* is an obligatory intracellular protozoan parasite responsible for human and animal toxoplasmosis. It belongs to the family Sarcocystidae, which also groups together other major pathogens of humans and of animals, such as *Neospora* or *Sarcocystis* (Levine, The Protozoan Phylum Apicomplexa. Vol. 1, CRC Press, Boca Raton, Fla., p. 203, 1988; Tenter et al., Int. J. Parasitol. 32(5): 595-616, 2002). Its life cycle has two distinct aspects: an "asexual" cycle in an intermediate host, such as humans, mice, ovine species and porcine species, resulting in the production of tachyzoites and then of cysts containing bradyzoites; and a "sexual" cycle in cats, resulting in the production of oocysts (containing sporozoites) eliminated in the feces.

Animal toxoplasmosis poses a considerable economic problem in the field of agricultural rearing. It affects all productive animals. Transmission to these animals takes place via the ingestion of oocysts, forms of resistance emitted into the environment by cats infected with a pathogenic toxoplasma. In ovine species, caprine species and porcine species infected during gestation, it causes abortions. In the European Union, the ovine population of which is estimated at 100 million heads, 1 million lambs are lost each year because of abortions due to toxoplasma.

Moreover, the consumption of meat (especially mutton and pork) infected with the presence of bradyzoites is the main source of human infections. When contracted during pregnancy, toxoplasmosis is the 2nd most common cause of congenital malformations. In addition, over the last twenty years, this parasite has emerged as an opportunistic pathogen, responsible for encephalitis in AIDS patients.

The development of vaccines conferring protection against Apicomplexa parasitoses is the subject of numerous research studies. Two main strategies are employed: 1) the identification of parasitic antigens capable of inducing a protective immune response, and the incorporation of these antigens into vaccine compositions; 2) the selection of attenuated parasite strains. For example, in the case of toxoplasmosis, it has been proposed to use various attenuated strains of *Toxoplasma gondii* (U.S. Pat. No. 5,045,313; U.S. Pat. No. 4,473,549; patent application US 2002/0164754; patent application GB 2 204 323) for conferring anti-toxoplasma immunity on mammals.

At the current time, a single anti-toxoplasmosis vaccine based on an attenuated strain is commercially available. It is the TOXOVAX vaccine (Schering-Plough), based on live tachyzoites of the S48 strain of *Toxoplasma gondii*. The nature of the mutation responsible for the attenuation of this strain remains unknown.

The key steps in Apicomplexa infection, and in particular infection with *Toxoplasma gondii*, are the attachment of the parasite to the host cells, followed by invasion of the latter. The invasive apparatus of the Apicomplexa involves the sequential exocytosis of two types of secretory organelles: micronemes and rhoptries.

Recent studies have demonstrated the central role of micronemes in the recognition of host cells, and the adhesion to the latter. The microneme proteins, referred to under the generic name "MICs" contain modules homologous to the adhesion domains of higher eukaryotic proteins (Tomley and Soldati, Trends Parasitol. 17: 81-88, 2001).

A dozen or so MIC proteins are currently known in *Toxoplasma gondii* (Soldati et al., Int. J. Parasitol. 31: 1293-1302, 2001). Some of them are transmembrane proteins, for example MIC2 of *Toxoplasma gondii*, called TRAP in *Plasmodium* (Matuschewski et al., EMBO J. 21: 1597-1606, 2002); the others are soluble proteins which are targeted to the micronemes and redistributed at the surface of the parasite during invasion, in combination with the transmembrane proteins.

Recently, two soluble proteins, MIC1 and MIC3, capable of binding to the surface of host cells, have been characterized in *T. gondii* (Achbarou et al., Mol. Biochem. Parasitol., 47, 223-233, 1991; Fourmaux et al., Mol. Biochem. Parasitol. 83: 201-210, 1996; Garcia-Reguet et al., Cell. Microbiol. 2: 353-364, 2002).

The MIC1 protein contains a tandem duplicated domain which has a distant homology with the TSP-1-type domain of TRAP, and exhibits a lactose-binding specificity (Lourenco et al., Glycobiol. 11: 541-547, 2001).

The MIC3 protein is a dimer with an apparent molecular weight of 90 kDa, formed from two subunits of 38 kDa connected by disulfide bridges. MIC3 contains five EGF-type domains, two of which are overlapping, and a domain of "chitin-binding domain" type, rich in disulfide bridges, and which appears to be necessary for binding to the surface of the host cell (Garcia-Reguet et al., 2000, mentioned above; Cerede et al., EMBO J. 21: 2526-2536, 2002).

MIC1 and MIC3 associate with other MIC proteins so as to form two independent complexes, MIC1/4/6 and MIC3/8. The transmembrane proteins MIC6 and MIC8 play the role of transporters for targeting respectively the MIC1/4 and MIC3 proteins to the micronemes. The MIC1 protein is essential for the MIC1/4/6 complex to be able to leave the early compartments of the secretion pathway (Reiss et al., J. Cell Biol. 152: 563-578, 2001).

It has recently been shown that the MIC3 protein of *Toxoplasma gondii* constitutes a major vaccine antigen which gives rise to an early and very strong humoral immune response (PCT application WO 01/64243).

With the aim of studying the role of MIC1 and MIC3 in the invasive capacity and the virulence of *Toxoplasma gondii*, the inventors have constructed mutant strains of *T. gondii*, in which one and/or the other of the adhesins MIC1 and MIC3 has/have been inactivated.

They have noted that the inactivation of MIC1 decreases by approximately 50% the invasive capacity with respect to fibroblasts in vitro, whereas the inactivation of MIC3 does not modify this invasive capacity; the simultaneous inactivation of the two proteins does not significantly modify the invasive capacity compared with the inactivation of MIC1 alone. The virulence in vivo is only very slightly affected by the isolated inactivation of MIC1 and MIC3; on the other hand, it is greatly decreased by the simultaneous inactivation of the two proteins.

The inventors have also noted that, despite the absence of the major antigens constituted by MIC1 and MIC3, a double mutant strain of *Toxoplasma gondii* in which these two proteins are inactivated makes it possible to obtain an effective vaccine protection with respect to toxoplasmosis.

They have subsequently undertaken to study the infectious and protective characteristics of said strain on animals, in particular on mice and ewes.

They have thus demonstrated that vaccination with this strain protects the animals against the formation of brain cysts when there is a re-infection with a pathogenic wild-type strain of *Toxoplasma gondii*, which considerably decreases the scope of an infection with this pathogenic wild-type strain, the risk of transplacental passage in the case of gestating females, and the possibility of transmission by consumption of meat of the immunized animals, and therefore, in the end, makes it possible to bring down the general prevalence of the infection.

A subject of the present invention is therefore a mutant strain of an Apicomplex of the family Sarcocystidae, comprising a mutation which inactivates the adhesin MIC1 and a mutation which inactivates the adhesin MIC3.

According to a preferred embodiment of the present invention, said Sarcocystidae is chosen from *Toxoplasma* and *Neospora*.

According to a preferred arrangement of this embodiment, said mutant strain is a strain of toxoplasma, in particular of *Toxoplasma gondii*.

Herein, the expression:
"mutation which inactivates the adhesin MIC1" is intended to mean any mutation resulting in the absence of expression of MIC1, or in the expression of a nonfunctional MIC1 protein, i.e. incapable of forming a complex with the MIC4 and MIC6 proteins, or incapable of binding lactose; and "mutation which inactivates the adhesin MIC3" is intended to mean any mutation resulting in the absence of expression of MIC3, or in the expression of a nonfunctional MIC3 protein, i.e. having lost its function of binding to the surface of a host cell.

Examples of mutations resulting in the absence of expression of MIC1 or MIC3 are in particular the deletion of the entire corresponding gene, or of its coding region, or of its promoter region. Examples of mutations resulting in the expression of a nonfunctional MIC3 protein are in particular mutations affecting the region of the mic3 gene encoding the domain of type: "chitin-binding domain of the MIC3 protein", i.e. amino acids 84-144 of said protein. They can in particular be mutations affecting at least the tryptophan at position 126 or the phenylalanine at position 128 of the MIC3 protein.

These mutations can be made conventionally by insertion, deletion or substitution of one or more bases in the targeted sequence.

By way of nonlimiting examples of mutagenesis and transformation techniques which can be used in toxoplasmas, mention will in particular be made of those described in the following publications: Kim et al., (Science 262: 911-914, 1993); Donald and Roos, (Mol. Biochem, Parasitol. 63: 243-253, 1994); Soldati et al., (Mol. Biochem. Parasitol. 74: 87-97, 1995); Donald and Roos, (Mol. Biochem. Parasitol. 91: 295-305, 1998).

A subject of the present invention is also the use of a mutant strain of Apicomplexa, and in particular of toxoplasma, in accordance with the invention, for obtaining a vaccine intended to confer protective immunity against an Apicomplexa parasitosis, in particular against toxoplasmosis.

A subject of the present invention is also a vaccine, characterized in that it comprises, as active ingredient, a mutant strain of Apicomplexa, and in particular of toxoplasma, in accordance with the invention, as defined above.

BRIEF DESCRIPTION OF THE DRAWINGS

FIG. 1: Western blot results using anti-MIC3 and anti-MIC1 monoclonal antibodies (1=wild-type strain of Toxoplasma gondii RH; 2=mutant mic3KO; 3=mutant mic3KO+MIC3; 4=mutant mic1KO; 5=mutant mic1KO+MIC1; 6=mutant mic1-3KO; 7=mutant mic1-3KO+Mic1-3).

FIG. 2: Number of parasitic vacuoles counted as the mean of vacuoles per field originating from 4 coverslips, on the basis of 5 independent repetitions (A: RHhxgprt⁻, mic1KO, mic3KO, mic1-3KO; B: RHhxgprt⁻, mic1KO, mic1KO+MIC1)

FIG. 3: Study of the virulence of the mic1KO, mic3KO, mic1-3KO, mic1KO+MIC1, mic3KO+MIC3 and mic1-3KO+Mic1-3 mutants (for FIGS. 3A, 3B and 3C, ♦=strain mic1KO (A); strain mic3KO (B); strain mic1-3KO (C); ■=strain mic1KO+MIC1 (A); strain mic3KO+MIC3 (B); strain mic1-3KO+Mic1-3 (C); Δ=strain RHhxgprt⁻).

FIG. 4: Expression of the MIC3 proteins in the various strains (4A=Western blotting; 4B=cell blotting; 1=wild-type strain of Toxoplasma gondii RH; 2=strain mic1-3KO+MIC3; 3=strain mic1-3KO+MIC3W126A; 4=strain mic1-3KO+MIC3F128A; 5=strain mic1-3KO+MIC3Y135A).

FIG. 5: Analysis of the virulence test (♦=strain mic1-3KO; ■=strain mic1KO; Δ=strain mic1-3KO+MIC3; o=strain mic1-3KO+MIC3Y135A; +=strain mic1-3KO+MIC3F128A; x=strain mic1-3KO+MIC3W126A).

FIG. 6: Post-immunization temperatures of the ewes of the various batches.

FIG. 7: Mean of the results of the ELISA assays for the sera of the various batches of ewes.

FIG. 8: Post-infection temperatures of the ewes of the various batches.

FIG. 9: Western blots using anti-MIC3 (T82C10) or anti-MIC1 (T101F7) monoclonal antibodies. (A) S48 tachyzoite lysate; (B) mic1-3KO tachyzoite lysate. Lane 1: anti-76K serum; lane 2: naive mouse serum; lane 3: anti-MIC1; lane 4: anti-MIC3.

FIG. 10: Post-immunization temperatures of the ewes of the various batches.

FIG. 11: Results of the ELISA assays for the sera of the various batches of ewes.

FIG. 12: Post-infection temperatures of the ewes of the various batches.

The present invention will be understood more clearly from the further description which follows, which refers to examples of construction of *Toxoplasma gondii* mutants in which MIC1 and/or MIC3 are inactivated, and of use, for a vaccine, of a double mutant in which MIC1 and MIC3 are inactivated.

It should be clearly understood, however, that these examples are given only by way of illustration of the subject of the invention, for which they in no way constitute a limitation.

EXAMPLE 1

Inactivation of MIC1 and/or MIC3 in *T. gondii*

Plasmids Used:

The plasmids pmic3KO-1 and pmic3KO-2 were used, respectively, to construct the single mutant mic3KO from the RHhxgprt⁻ strain and the double mutant mic1-3KO from the mic1KO strain. The plasmids pM3MIC3ty and pM2MIC1myc+pM3MIC3 were used, respectively, to restore the expression of MIC3 in the mic3KO mutant (strain mic3KO+MIC3), and to restore the expression of MIC1 and MIC3 in the double mutant mic1-3KO (strain mic1-3KO+MIC1-3).

Plasmid pmic3KO-1

The 3'UTR region of the MIc3 gene (2136 bp) was amplified by PCR from the plasmid pBlueMIC3 (Cerede et al., 2002, mentioned above), which results from the insertion of a genomic DNA fragment of 2247 bp (GenBank AJ132530) of *T. gondii* at the NotI site of the plasmid pBluescript II® SK(−).

For the amplification, the primers ML9: 5'-GTGTAAGCT-TCAGCGAGTCTCTGAGAG-3' (SEQ ID NO: 1) and ML10: 5'-GGGGTACCGAGCTCATGAGCAGAAGCT-GCCAG-3' (SEQ ID NO: 2) were used. The amplified region was cloned between the HindIII and KpnI restriction sites of the plasmid pminiHXGPRT (Donald and Roos, 1998, mentioned above). A DNA fragment of 1977 bp of the 5'UTR region of Mic3 was obtained by XbaI/NheI digestion of an EcoRI fragment of 3.5 kb of the 5' genomic sequence of Mic3, and cloned into the XbaI site of pminiHXGPRT.

The resulting plasmid, which contains the HXGPRT (hypoxanthine-xanthine-guanine phosphoribosyl transferase) selection marker, bordered by the regions flanking, in the 3' position and 5' position, the ORF of mic3, was called pmic3KO-1.

Plasmid pmic3KO-2

The 3'UTR and 5'UTR regions of mic3, obtained as described above, were inserted into the plasmid pTUB/CAT (Kim et al., 1993, mentioned above), on either side of the sequence encoding the chloramphenicol acetyl transferase (CAT) selection marker, at the same restriction sites as those described for the plasmid pmniHXGPRT.

The resulting plasmid, containing the CAT selection marker, bordered by the regions flanking, in the 3' position and 5' position, the ORF of mic3, was called pmic3KO-2.

Plasmid pM3MIC3ty

This plasmid was constructed from the plasmid pT8GFPPfmyoAtail (Hetmann et al., Mol. Biol. Cell 11: 1385-1400, 2000), in which a TY epitope (Bastin et al., Mol. Biochem. Parasitol. 77(2): 235-239, 1996) has been added between the NsiI and PacI sites. This plasmid contains the tubulin promoter between the KpnI and EcoRI sites of the gene encoding GFP, bordered by the EcoRI and NsiI sites.

The Mic3 promoter region (562 bp) was amplified by PCR from the plasmid pBlueMIC3 with the primers ML23: 5'-CT-GAATTCAGATCTTACCAGTGTTGGACAAGG-3' (SEQ ID NO: 3) and ML24: 5'-GGGGTACCCCTTGCTAGG-TAACCACTCGTGC-3' (SEQ ID NO: 4), and inserted in place of the tubulin promoter at the KpnI and EcoRI sites.

The primer ML24 makes it possible to introduce a BglII restriction site upstream of the EcoRI site and to then clone the Mic3 gene in place of the gene encoding GFP at the BglII and NsiI sites.

The sequence encoding MIC3 was amplified by PCR from the plasmid pBlueMIC3 with the primers
ML11: 5'-GCACAATTGAGATCTAAAATGCGAG-GCGGGACGTCC-3' (SEQ ID NO: 5) and
ML15: 5'-TGCTATGCATTCCTAGGCTGCT-TAATTTTCTCACACGTCAC-3' (SEQ ID NO: 6) introducing, respectively, the BglII and NsiI restriction sites.

Plasmids pM2MIC1myc and pM3MIC3

The plasmid pM2MIC1myc (Reiss et al., J. Cell Biol. 152: 563-578, 2001) expresses the MIC1 protein, tagged with the myc epitope at its C-terminal end, under the control of the sequences flanking, in the 5' position and 3' position, the Mic2 gene.

The plasmid pM3MIC3 was constructed by cloning a PvuI/SacI fragment of 2072 bp of the vector pBlueMIC3, containing the Mic3 gene and its 5' and 3' flanking regions, between the SacI and PacI sites of the vector pT/230-TUB5/BLE (Soldati et al., Mol. Biochem. Parasitol. 74: 87-97, 1995) containing an expression cassette expressing the phleomycin selection marker.

Construction of the Mutant Strains mic3KO and mic1-3KO, and of the Complemented Mutant Strains mic3KO+MIC3 and mic1-3KO+MIC1-3

The haploidy of the Apicomplex genome during the proliferative phase makes it possible to knock out the Mic3 gene in a single homologous recombination.

All the *T. gondii* used were produced in human fibroblasts (HFFs) cultured in Dulbecco's minimal medium (DMEM) supplemented with 10% of fetal calf serum (FCS), 2 mM glutamine, 50 U/ml of penicillin and 50 μg/ml of streptomycin. They were harvested during lysis of the host cells.

Strain mic3KO

The *T. gondii* strain used for the mutagenesis is the RHhxgprt⁻ strain (Donald and Roos, 1998, mentioned above), deficient for the hypoxanthine-xanthine-guanine phosphoribosyl transferase (HXGPRT) gene, and as a result, sensitive to mycophenolic acid.

80-100 μg of plasmid pmic3KO-1 purified and then linearized with KpnI were added to $10^7$ RHhxgprt⁻ tachyzoites suspended in Cytomix electroporation medium (van den Hoff et al., Nucleic Acids Res. 20: 2902, 1992), and the electroporation was carried out in a 4 mm-gap cuvette, in a volume of 800 μl, on a BTX Electrocell Manipulator device (parameters: 2 kV, R=48 ohms).

After electroporation, the tachyzoites were deposited onto a monolayer of HFF cells in culture. For selection of the mutants, the day after the electroporation, the culture medium was supplemented with the selection agent (25 μg/ml of mycophenolic acid and 50 μg/ml of xanthine) and three passages in culture were carried out in this medium.

Five days after the final passage, the parasites are cloned by limiting dilution, in the wells of a 96-well plate, of HFF cells, in the presence of selection agent, and the clones selected are amplified.

Strain mic1-3KO

The *T. gondii* strain used for the mutagenesis is the mic1KO strain (Reiss et al., J. Cell Biol. 152: 563-578, 2001), which derives from the RHhxgprt⁻ strain described above, by deletion of the Mic1 gene, replaced with the gene encoding HXGPRT in the mic1KO strain.

80-100 μg of plasmid pmic3KO-2 purified and then linearized with KpnI were added to $10^7$ mic1KO tachyzoites for an electroporation under the conditions described above.

The mutants were selected and cloned as described above, in the presence of 20 μM of chloramphenicol as selection agent.

The mutants in which MIC3 was inactivated are called mic3KO, and those in which MIC1 and MIC3 were inactivated are called mic1-3KO.

Strain mic3KO+MIC3

The expression of MIC3 was restored by cotransfection of the mic3KO parasites with 100 μg of the vector pM3MIC3ty, and 10 μg of the plasmid pTUB/CAT.

The selection was carried out in the presence of 20 μM of chloramphenicol as described above.

The mic3KO strain complemented with MIC3 is called mic3KO+MIC3.

Strain mic1-3KO+MIC1-3

The expression of MIC1 and MIC3 was restored by cotransfection of the mic1-3KO parasites with 100 μg of the vector pM2MIC1myc, and 10 μg of the plasmid pM3MIC3.

The mutants were selected and cloned as described above, in the presence of 10 μg/ml of phleomycin as selection agent.

The mic1-3KO strain complemented with MIC1 and MIC3 is called mic1-3KO+Mic1-3.

The total proteins of the mutants mic3KO, mic1-3KO, mic3KO+MIC3, and mic1-3KO+Mic1-3 were analyzed by SDS-PAGE electrophoresis and Western blotting. After extraction of the total proteins by boiling of the cells in SDS buffer (in the absence or presence of 0.1M DTT) and separation on 10% polyacrylamide gels, the proteins were transferred onto a nitrocellulose membrane. The Western blots were labeled as described by Garcia-Reguet et al. (1998, mentioned above) using anti-MIC3 (T42F3 at 1:400) and anti-MIC1 (T101F7) monoclonal antibodies and then detected with goat anti-mouse IgGs conjugated to alkaline phosphatase (1:1000).

The results are presented in FIG. 1.

Legend of FIG. 1:
1=wild-type strain of *Toxoplasma gondii* RH
2=mutant mic3KO
3=mutant mic3KO+MIC3
4=mutant mic1KO (Reiss et al., 2001)
5=mutant mic1KO+MIC1 (Reiss et al., 2001)
6=mutant mic1-3KO
7=mutant mic1-3KO+Mic1-3

The results show that the expression of MIC3 is undetectable in mic3KO (2) and mic1-3KO (6), but is restored in mic3KO+MIC3 (3) and mic1-3KO+MIC1-3 (7). The expression of MIC1 is undetectable in mic1KO (4) and mic1-3KO (6), but is restored in mic1KO+MIC1 (5) and mic1-3KO+Mic1-3 (7).

These results were confirmed by immunofluorescence. The tachyzoites cultured overnight on a monolayer of HFF cells were washed in PBS and fixed with 4% formaldehyde for 20 min. After 3 washes, the infected HFF cells were permeabilized with 0.1% of Triton X-100 in PBS for 10 min, the reaction was stopped with 10% of fetal bovine serum (FBS) for 30 min, and the cells were then incubated with the primary antibody (anti-MIC1 mAb T101F7, anti-MIC3 mAb T42F3) diluted in 2% FBS, for 40 min, washed, and then incubated with a secondary antibody (goat anti-mouse coupled to FITC, and Texas red goat anti-rabbit). The observations were made under a Leica DMRA2 microscope equipped for epifluorescence and the images were recorded with a Princeton coolSNAP CCD camera.

The results show that no MIC3 protein is detectable in mic3KO tachyzoites, whereas an expression of wild-type MIC3 is observed in the micronemes of the complemented strains (mic3KO+MIC3, mic1-3KO+Mic1-3). The complementation of MIC1 in mic1KO+MIC1 and mic1-3KO+ MIC1-3 results in a certain accumulation of MIC1 in the parasitophorous vacuole and in the perinuclear space.

EXAMPLE 2

Effects of the Inactivation of MIC1 and/or MIC3 on the Infectious Properties of *T. gondii*

The *Toxoplasma gondii* mutants described in example 1 above were maintained by regular passages on HFF cells cultured in DMEM medium supplemented with 10% of fetal calf serum (FCS), 2 mM glutamine, 50 U/ml of penicillin and 50 μg/ml of streptomycin.

Invasive Capacity $2 \times 10^5$ purified mic1KO, mic1KO+MIC1, mic3KO and mic1-3KO tachyzoites were added to HFF cells cultured on glass coverslips. The cells were fixed for 12 h and then stained using a methylene blue-eosin mixture (RAL 555 kit), and mounted under coverslips, permanently (Pertex, Microm, France). The number of parasitic vacuoles, representing the invasive capacity of the parasite, was counted in 10 randomly selected fields per coverslip, and the data were presented as the mean of vacuoles per field originating from 4 coverslips, on the basis of 5 independent repetitions.

The control was carried out under the same conditions with the RHhxgprt⁻ strain, the invasive capacity of which is comparable to that of the wild-type RH strain of *Toxoplasma gondii*.

Figure 2:
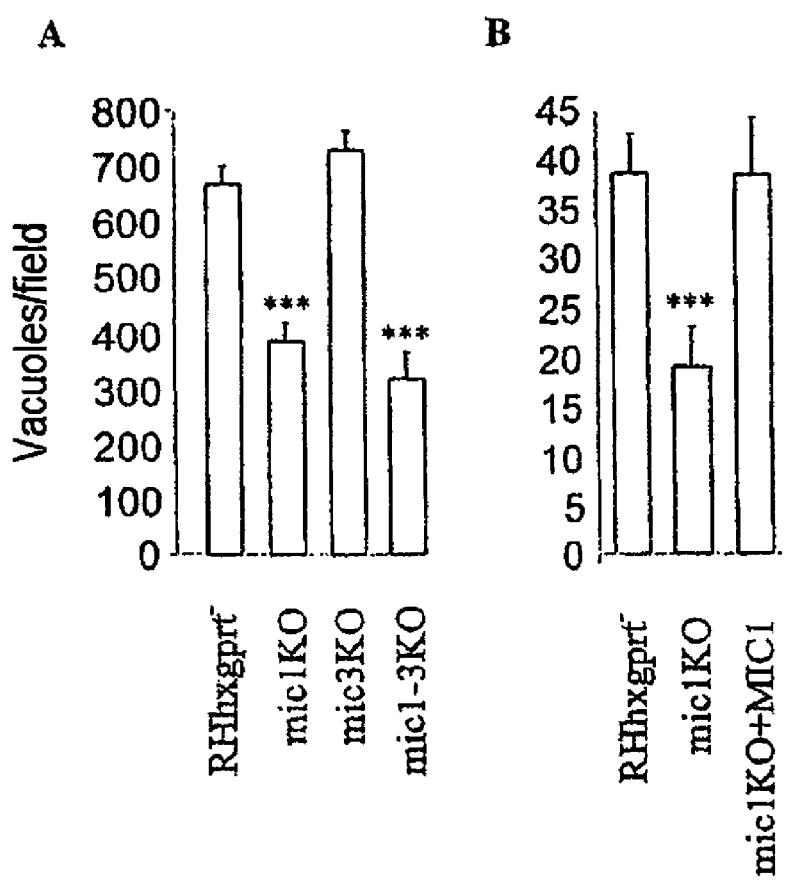

The results are presented in FIG. 2 (***=significantly less invasion, $p<0.001$).

The results show that the invasive capacity of the mic1KO parasites is decreased by approximately 50% compared with that of the control strain RHhxgprt⁻.

On the other hand, the invasive capacity of the mic3KO parasites and of those of the control strain is comparable (FIG. 2A). The invasive capacity of the mic1-3KO parasites is not significantly different from that of the mic1KO mutants (FIG. 2A), indicating that MIC1 and MIC3 do not have an additive function in the invasion of fibroblasts by *Toxoplasma gondii*.

The complementation of mic1KO by MIC1 restores the invasive capacity to a level comparable to that of the control strain (FIG. 2B).

Virulence

The mice generally die 9 days after an intraperitoneal infection with 20 tachyzoites of the wild-type strain RH of *Toxoplasma gondii*.

The study of the virulence of the mic1KO, mic3KO, mic1-3KO, mic1KO+MIC1, mic3KO+MIC3 and mic1-3KO+ Mic1-3 mutants was carried out on a batch of 10 male OF1 mice, by intraperitoneal injection of 20 tachyzoites/mouse of the mic1-3KO strain, and by following the outcome regarding the infected mice.

The controls were carried out under the same conditions on a batch of 9 male OF1 mice, using the RHhxgprt⁻ strain, the virulence of which is comparable to that of the wild-type strain RH of *Toxoplasma gondii*.

Figure 3:
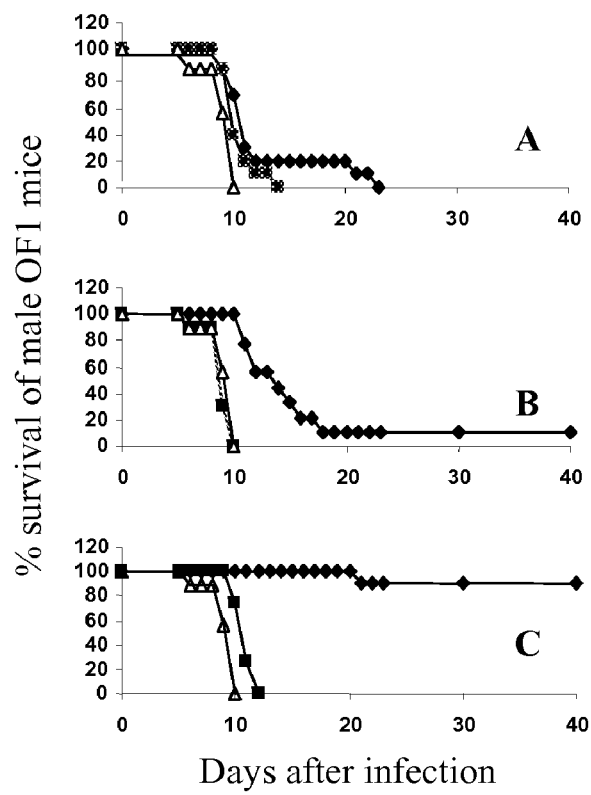

The results are represented in FIG. 3.

Legend of FIGS. 3A, 3B and 3C:
◆=strain mic1KO (A); strain mic3KO (B); strain mic1-3KO (C),
■=strain mic1KO+MIC1 (A); strain mic3KO+MIC3; strain mic1-3KO+Mic1-3 (C),
Δ=strain RHhxgprt⁻ (A, B and C).

All the mice infected with the RHhxgprt⁻ strain died 9 days after the infection. The mice infected with mic1KO or mic3KO exhibit a slight delay in mortality (death of the mice between 9 and 22 days after infection), which is not observed in the case of the mice infected with the complemented mutants mic1KO+MIC1 and mic3KO+MIC3. Just one of the mice infected with mic3KO remained alive 44 days after infection, and this animal developed a *T. gondii*-specific antibody response (results not shown). These results indicate that the isolated inactivation of the Mic1 or Mic3 gene results in only a slight decrease in virulence in the mice.

On the other hand, in the case of the mice infected with the mic1-3KO strain, a virtually complete survival (90% survival 40 days after infection) is observed. The complementation of mic1-3KO with MIC1 and MIC3 (strain mic1-3KO+Mic1-3) completely restores the virulence of the parasites.

The mice were also infected with various amounts of the double mutant mic1-3KO and the lethal dose (LD100) of mic1-3KO was compared with that of the control strain RHhxgprt⁻. While the LD100 at 9 days of the control strain is less than 20 tachyzoites, that of the mic1-3KO strain is of the order of $2\times10^3$ tachyzoites.

EXAMPLE 3

Involvement of the Adhesion Function of MIC3 in the Virulence of *Toxoplasma gondii*

Determination of Residues Involved in the Adhesion Function of MIC3

It has been shown (Cerede et al., 2002, mentioned above) that the "chitin-binding-type domain" of MIC3 is essential for binding to the surface of the host cell. Various mutations were introduced into this domain, in order to determine the residues essential to the functionality of MIC3.

The mutations made are as follows:
substitution of one of the cysteine residues at positions 102 (mutant C102G), 107 (mutant C107G) and 108 (mutant C108G), with a glycine residue;
substitution of the proline residue at position 103 with an alanine residue (mutant P103A);
substitution of one of the serine residues at positions 109 (mutant S109A) and 130 (mutant S130A) with an alanine residue;
substitution of one of the tyrosine residues at positions 96 (mutant Y96A), 135 (mutant Y135A) and 141 (mutant Y141A), with an alanine residue;
substitution of one of the phenylalanine residues at positions 97 (mutant F97A), 121 (mutant F121A) and 128 (mutant F128A), with an alanine residue;
substitution of the tryptophan residue at position 126 with an alanine residue (mutant W126A).

The positions of the mutations are indicated with reference to the polypeptide sequence of the precursor of MIC3 (Genbank CAB56644).

The mutations were created by site-directed mutagenesis by PCR (QUICKCHANGE, Stratagene) of the sequence encoding the mature form of MIC3, contained in the plasmid pOC2 (Cerede et al., 2002, mentioned above).

The plasmids obtained are respectively called pC102 (mutant C102G), pC107 (mutant C107G), pC108 (mutant C108G), pP103 (mutant P103A), pS109 (mutant S109A), pS130 (mutant S130A), pY96 (mutant Y96A), pF97 (mutant F97A), pF121 (mutant F121A), pW126 (mutant W126A), pF128 (mutant F128A), pY135 (mutant Y135A), and pY141 (mutant Y141A).

The plasmids were purified using the QIAGEN KIT (Qiagen), and the presence of the expected mutations was verified by sequencing.

The mutant MIC3 proteins were expressed by transfection of BHK-21 cells (Baby Hamster Kidney, ATCC CCL-10) cultured in BHK-21 medium (Gibco-BRL) supplemented with 5% fetal calf serum (FCS), 2 mM of tryptose, 100 U/ml of penicillin and 100 µg/ml of streptomycin.

For each plasmid, $3\times10^5$ BHK-21 cells, cultured beforehand on coverslips for 24 h in 24-well plates, were transfected with the purified plasmid, using LIPOFECTAMINE, according to the conditions recommended by the manufacturer (Gibco-BRL). The cells were cultured for a further 24 h before analysis.

The binding properties of the mutant MIC3 proteins were studied by analyzing their localization in the transfected BHK-21 cells. The transfected BHK-21 cells were fixed with 3% paraformaldehyde in PBS for 15 min, and then washed and permeabilized with 0.1% of Triton X-100 in PBS for 10 min. The coverslips bearing the cells were then washed in PBS containing 0.5% of BSA, and incubated for 1 h in the same buffer containing an anti-MIC3 antibody (T82C10, 1:200) or anti-V5 antibody (1:500), and then for 1 h with a goat IgG conjugated to TRITC (Sigma, 1:400), with several washes in PBS between each incubation. The coverslips were then washed and mounted on microscope slides. The visualization was carried out using an epifluorescence microscope.

Four categories of mutants were defined according to their localization.

In the first category (mutants C102G, C107G, C108G, Y141A, F121A), the protein is retained in the secretory system; in the second category (Y135A, Y96A, F97A, S109A, P103A), the protein is secreted normally and binds to the surface of the transfected cells, as does the mature wild-type MIC3 protein; in the third category (W126A, Y128A), the protein is secreted normally but does not bind to the surface of the transfected cells; in the fourth category (S130A), the protein is secreted normally and binds to a network of cellular material deposited by the cells at the surface of the glass plates.

These results show that all the mutations affecting a cysteine residue result in a major secretion deficiency; the corresponding mutant MIC3 proteins accumulate in the form of large perinuclear vesicles, indicating that these proteins are incorrectly folded or incompletely assembled. This result is coherent with the role of cysteines in the folding of the domain.

As regards the other substitutions, the two mutations F121A and Y141A also affect the leaving of the proteins. The other mutants (Y135A, Y96A, F97A, S109A, P103A, W126A, F128A, S130A) are all expressed in dimer form and secreted. Two of them (W126A, Y128A) do not bind to the transfected BHK-21 cells. Due to the loss of these binding properties, these two mutants are abundantly secreted into the supernatant. In the case of the S130A mutant, the labeling with the anti-MIC3 antibodies is not associated with the plasma membrane of the transfected cell, as in the case of the wild-type MIC3 protein, but with the intercellular space, as if the R-MIC3 S130A protein was bound to the cellular material deposited onto the plates.

These results show that the two aromatic residues W126 and Y128 are involved in the interaction with the receptor of the host cell's surface, and that the residue S130 could also contribute to the binding properties of MIC3 by participating in the specificity of interaction.

Involvement of the Residues W126 and Y128 in the Virulence of *T. gondii*

To study the role of the adhesion function of MIC3 in the virulence of *T. gondii*, experiments consisting of complementation of the double mutant strain mic1-3KO with the mutants W126A and F128A were carried out.

The plasmids pM3MIC3W126A, pM3MIC3F128A and pM3MIC3Y135A were constructed from the plasmid pM3MIC3. These plasmids bear the phleomycin selection gene, and express the mutants W126A, F128A and Y135A, respectively. The presence of the expected mutations was verified by sequencing.

The mic1-3KO strain was transfected with the plasmid pM3MIC3W126A (strain mic1-3KO+MIC3W126A) or pM3MIC3F128A (strain mic1-3KO+MIC3F128A). The strain mic1-3KO+MIC3 and the strain mic1-3KO transfected with the plasmid pM3MIC3Y135A (mic1-3KO+MIC3Y135A) were used as positive binding controls.

The expression of the MIC3 proteins in the various strains was analyzed by Western blotting, and their binding properties were analyzed by cell blotting. The cell blotting was carried out with a duplicate of the nitrocellulose sheet used for the Western blotting, incubated with a suspension of Mode-K cells (Vidal et al., J. Immunol. Methods 166: 63-73, 1993) cultured in RPMI medium (Bio Whittaker) supplemented with 5% of fetal calf serum (FCS), 25 mM of Hepes, 2 mM of glutamine, 100 U/ml of penicillin and 100 µg/ml of streptomycin.

Figure 4:
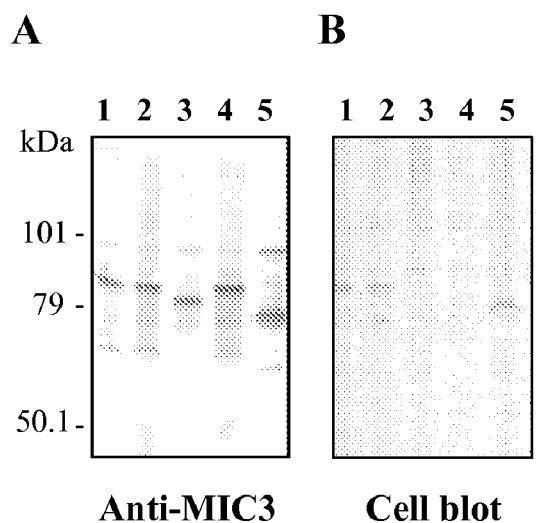

The results are presented in FIGS. 4A (Western blotting) and 4B (cell blotting).

Legend of FIGS. 4A and 4B:
1=wild-type strain of *Toxoplasma gondii* RH
2=strain mic1-3KO+MIC3
3=strain mic1-3KO+MIC3W126A
4=strain mic1-3KO+MIC3F128A
5=strain mic1-3KO+MIC3Y135A The results of the Western blotting show the expression of MIC3 proteins in all the strains. All these proteins migrate at the size expected for a dimer under reducing conditions. However, the W126A and Y135A proteins migrated faster than the others, which suggests a conformational modification.

The results of the cell blotting show that, as expected, the cells bind strongly to native MIC3 (1), MIC3myc (2) and to MIC3Y135A (5). On the other hand, the cells are incapable of binding to MIC3 W126A (3) and MIC3 F128A (4). Furthermore, the conformational modification of MIC3 Y135A does not affect its binding properties.

The strains mic1-3KO+MIC3W126A, mic1-3KO+MIC3F128A and, as a control, mic1-3KO+MIC3Y135A were used to analyze the involvement of the adhesion function of MIC3 in the virulence in mice.

Analysis of the Virulence of the Strains

The virulence test was carried out as described in example 2: 20 tachyzoites of each parasite were injected intraperitoneally into male OF1 mice (batch of 11 to 20 mice), the survival of which was followed for 40 days. The results are presented in FIG. 5.

Figure 5:
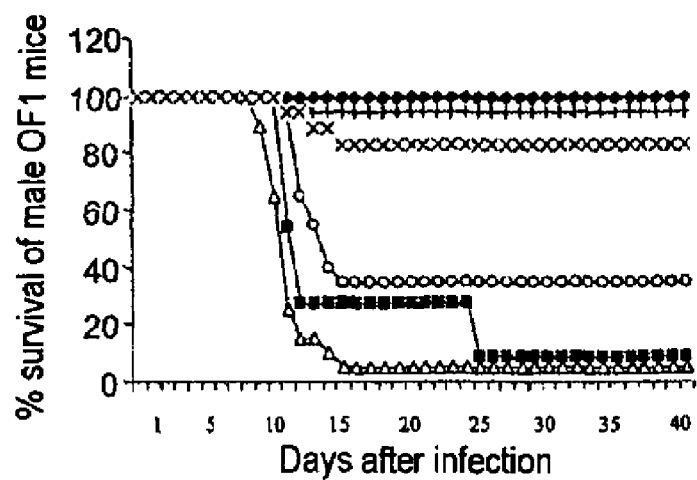

Legend of FIG. 5:
♦=strain mic1-3KO
■=strain mic1KO
Δ=strain mic1-3KO+MIC3
o=strain mic1-3KO+MIC3Y135A
+=strain mic1-3KO+MIC3F128A
×=strain mic1-3KO+MIC3W126A.

As expected, the mice infected with mic1-3KO+MIC3 behave in the same way as the mice infected with mic1KO, and die according to similar kinetics in 9-26 days. The survival of the mice infected with the strain mic1-3KO+MIC3Y135A is greater (which may be due to a partially defective targeting of the MIC3 Y135A protein into the parasitophorus vacuoles).

On the other hand, a survival of respectively 83.3% and 95% of the mice infected with the strain mic1-3KO+MIC3W126A and mic1-3KO+MIC3F128A is observed 40 days after infection.

These results show that the host-cell-binding function of MIC3 is essential for the virulence of the parasite.

EXAMPLE 4

Immunization of Mice with the MIC1-3KO Mutant

Experimental Protocol

Batches of 9.5-week old male OF1 mice were treated as follows:
  21 mice (batch 1) received the mic1-3KO mutant;
  21 mice (batch 2) received the mic1-3KO mutant and were then reinfected approximately 1 month later with the cystogenic *Toxoplasma gondii* strain 76K;
  10 mice (batch 3) were infected with the cystogenic *Toxoplasma gondii* strain 76K at the time of the reinfection of batch 2.

At D0, the mice of batches 1 and 2 received 20 tachyzoites of the mic1-3KO mutant intraperitoneally.

At D14, the infection of the mice was verified by searching for the presence of anti-*Toxoplasma gondii* IgGs, using total extract of toxoplasma (strain RH).

At D37, the mice effectively immunized (presence of anti-toxoplasma IgGs) of batch 2 (8 mice) and of batch 3 (8 mice) were fed by gavage with 70 cysts of the *Toxoplasma gondii* strain 76K.

At D61, the mice of the three batches were sacrificed. The presence of anti-MIC3 IgG, due to the infection with *Toxoplasma gondii* 76K (since the mic1-3KO vaccine strain does not express this protein), was sought and the brain cysts were counted in the ground brain material from these mice (counting on a Malassez cell; detection limit is 30 cysts per brain).

Eight 15-week-old naïve OF1 male mice were fed by gavage with ⅓ of the brain from each of the 8 mice of batch 2 (control for the absence of brain parasites). A control mouse received 60 cysts of the *Toxoplasma gondii* strain 76K derived from a mouse of batch 3 (positive control).

At D82, the presence of anti-MIC3 IgGs was sought in the mice fed by gavage at D61.

At D103, the mice were sacrificed and the brain cysts were counted.

Results

At D14

Out of the 42 mice of batches 1 and 2, 8 died around D10, during the acute phase of infection (which reflects the high sensitivity of the mice to the residual virulence of the MIC1-3KO mutant). The verification of infection by detection of IgGs directed against the parasitic antigens shows that 16 mice are negative and therefore uninfected. Batches 1 and 2 are therefore reduced to 10 and 8 mice, respectively.

At D61

Search for Anti-MIC3 IgGs

No anti-MIC3 IgG was detected in the serum of the mice of batch 1 (negative control), whereas the presence of anti-MIC3 IgG was detected in the serum of the mice of batch 3 (positive control). The presence of anti-MIC3 IgG was detected in the serum of the mice of batch 2, with the exception of one mouse, which exhibits a very weak response.

Counting of Brain Cysts

Upon microscopic examination, the brains of the mice of batch 1 do not contain any brain cysts (negative control), whereas brains from the mice of batch 3 contain from 2250 to 7250 cysts/brain, i.e. an average of 4037 cysts/brain (positive control). In the mice of batch 2, 7 mice do not contain any brain cysts and one mouse contains 30 brain cysts (i.e. a single cyst observed out of 16 counts of 10 µl on a Malassez cell).

At D82

The naïve mice fed by gavage with the brains from the mice of batch 2 exhibit anti-MIC3 IgGs. The control mouse which received 60 cysts of the *Toxoplasma gondii* strain 76K derived from a mouse of batch 3 also exhibits anti-MIC3 IgGs.

At D103

The naïve mice fed by gavage with the brains from the mice of batch 2 exhibit, respectively, 500, 375, 1000, 250, 165, 125, 310 and 375 brain cysts. By way of comparison, the control mouse which received 60 cysts of the *Toxoplasma gondii* strain 76K exhibits 2250 brain cysts.

Conclusion

The mice immunized with the mic1-3KO mutant form virtually no brain cysts during a re-infection with the *Toxoplasma gondii* strain 76K (99.9% protection).

On the other hand, several of the brains of reinfected mice are infectious, orally, and therefore the immunization with the mic1-3KO vaccine strain is not completely sterilizing when there is a reinfection.

EXAMPLE 5

Immunization of EWES with the MIC1-3KO Mutant

Animals

The immune status with respect to toxoplasmosis was determined on more than seventy ewes of the "pré-alpes du sud" race. Only thirty-six ewes were retained for the experiment because they were seronegative with respect to toxoplasmosis.

The ewes are maintained throughout the experiment in airtight housing on the site of the INRA of Nouzilly (Indre-et-Loire) in order to limit as much as possible the risks of natural contamination. Only the animal-care personnel and those carrying out experiments, equipped with clothing for inside the housing, can enter the buildings, in order to avoid contamination of the environment, and they leave the airtight zone only after having showered. The utensils used and the biological material leave only after having been passed through a disinfecting bath, and the manure is incinerated.

After immunization, the ewes are entered into reproduction by natural servicing after synchronization of their periods on heat using sponges impregnated with hormones and placed in the vagina of the ewes.

*T. gondii* Strains:

RH Strain

The production of total parasitic extract (ET) is carried out using the virulent RH strain (type I). The latter is maintained by successive passages on female OF1 mice by means of intraperitoneal injection of $10^6$ tachyzoites. Three days later, the mice are sacrificed and the tachyzoites are recovered by washing the intraperitoneal cavity with 5 mL of RPMI medium. The tachyzoites are counted on a Malassez cell, and $10^6$ tachyzoites are re-injected intraperitoneally into healthy mice in order to maintain the strain.

For the preparation of the total parasitic extract, the tachyzoites of the RH strain are washed, sonicated at 60 watts/s, three times for 10 min, and centrifuged at 2000 g for 30 min at 4° C. The supernatant is concentrated and aliquoted. The concentration is determined using an assay kit (Micro BGA), which uses BSA (bovine serum albumin) as standard. The aliquots are conserved at −20° C.

Mic1-3KO Vaccine Strain

The Mic1-3KO strain was obtained as described in example 1 above. It is maintained by successive passagrs on a line of human foreskin fibroblasts (HFF) cultured in IMDM medium to which are added 10% fetal calf serum, 50 mM of glutamate, 50 mM of penicillin and 50 mM of streptomycin.

PRU Challenge Strain

The ewes are infected mid-gestation with 400 oocysts of the PRU type II strain (Prugniaud strain) produced from purified feces of infected cats.

Experimental Protocol

Immunization

The thirty-six seronegative ewes were divided up into three batches of twelve ewes:
control batch
batch which receives $10^5$ Mic1-3KO tachyzoites, called "low dose batch" (KO FA)
batch which receives $2\times10^6$ Mic1-3KO tachyzoites, called "high dose batch" (KO FO).

The immunization of these ewes was carried out subcutaneously.

Temperature Recordings

After immunization, the rectal temperature of the animals was recorded daily each morning until it stabilized again at physiological values. The physiological temperature in ewes is 38.5° C. In order to take into account the activity of the animals and the stress engendered by the handling, hyperthermia is considered to exist starting from a temperature of 40.0° C.

Study of the Humoral Response

The humoral immune response was studied by evaluating, by ELISA, the kinetics of appearance of specific anti-*T. gondii* IgGs in the serum.

Obtaining the Sera

Serum samples are taken before immunization (D0) and then at D24, D39, D98 and D134 post-immunization.

Blood samples are taken from the jugular vein and the sample (without anticoagulant) is left overnight at +4° C. so as to allow the formation of the clot. The serum is recovered by centrifuging the samples at 1500 rpm for 5 min at +20° C. The supernatant is recovered and aliquoted in samples of 3 ml and conserved at −20° C.

ELISA Assay

The total extract of the *T. gondii* strain RH, obtained as described above, is used to coat the flat-bottomed wells of microtitration plates (Nunc). 100 µl of extract (at a concentration of 10 µg/ml in 50 mM carbonate buffer, pH=9.6) are placed in each well. After overnight incubation at +4° C., three washes are carried out in PBS buffer supplemented with 0.05% Tween-20 (PBS-T) using an automatic washer (MultiWash Advantage).

The nonspecific sites are saturated by incubation of the plates for 1 h 30 at 37° C. (humid atmosphere) with PBS containing 4% of BSA.

100 µl of each serum sample diluted in PBS-T (dilutions to 1/50 and to 1/100) are deposited, followed by incubation for 1 h at 37° C.

After two series of three washes, 100 µl of anti-sheep IgG coupled to alkaline phosphatase (AP; Sigma), diluted to 1/5000 in PBS-T, are deposited, followed by incubation for 1 h 30 at 37° C. Two further series of three washes are performed and the visualization is carried out using 100 µl of para-nitrophenylphosphate (PNPP) at 1 mg/ml in DEA-HCl.

The reading is carried out after 10 to 20 minutes of incubation, on a plate reader (Wallac 1420 Multilabel counter) at the wavelength $\lambda=405$ nm.

The accepted positivity threshold was determined according to the absorbance values (OD) of the ewes of the control batch: it is fixed at 0.35 of OD for a 1/100 serum dilution.

Infection

Females were placed into reproduction two months post-immunization. At mid-gestation, the gestating females were infected by gavage with 400 oocysts of the PRU strain. For the days following infection, the rectal temperature was taken daily, until it returned to physiological values, and the humoral and cellular immune response was evaluated as indicated above.

Finally, the febrile and infectious abortions were recorded during the lambing of the ewes.

Results

Post-Immunization Temperature Recordings

Figure 6:
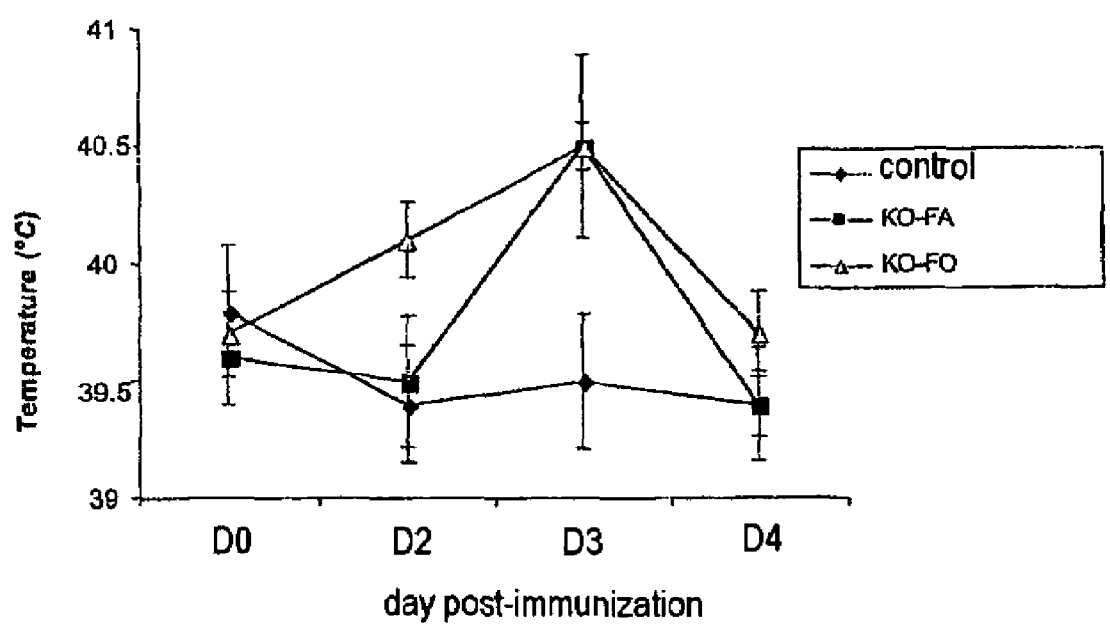

The means of the post-immunization temperatures of the ewes of the various batches are represented in FIG. 6.

The temperatures of the control batch remain physiological. On the other hand, a thermal peak at D3 is observed for the two immunized batches (40.5° C.); the hyperthermia of the FO batch is earlier (40.1° C. at D2) than that of the FA batch (39.5° C. at D2). A return of the temperatures to physiological values is observed 4 days after immunization.

Study of the Post-Immunization Humoral Response

Figure 7:
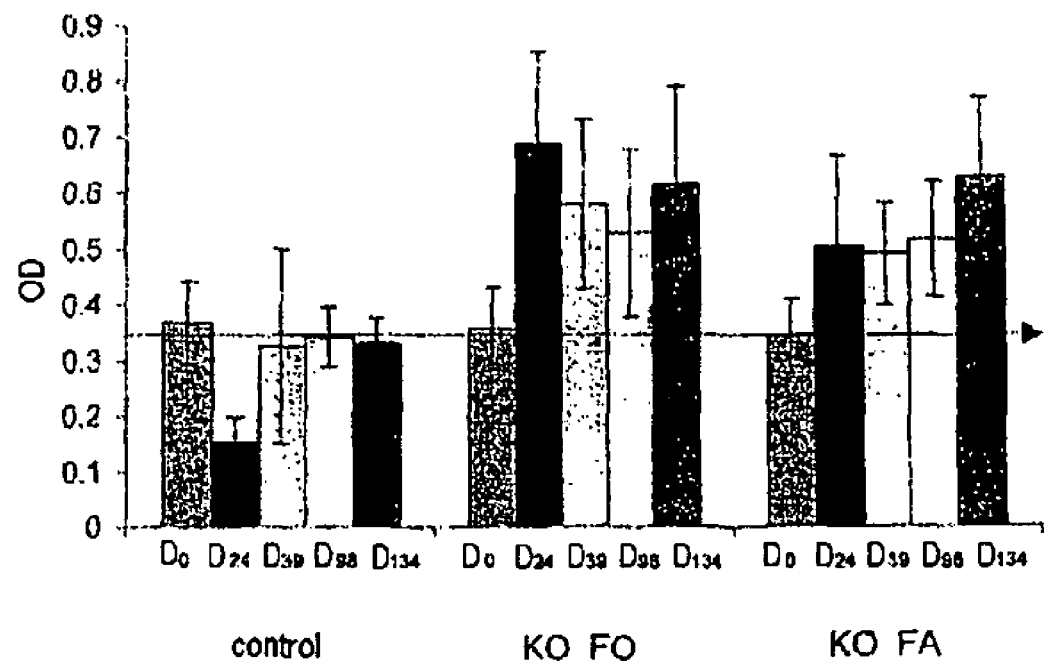

The means of the results of the ELISA assays at D0, D24, D39, D98 and D134 for the sera of the various batches of ewes, diluted to 1/100, are represented in FIG. 7.

The ewes of the control batch did not develop any humoral response.

The ewes of the FO batch and of the FA batch developed an anti-toxoplasma IgG response from D24. It is observed that this response is maintained up to the end of the experiment (D134).

Gestation Yield

After servicing by the male, out of the initial thirty-six ewes, only thirty were in gestation. Two non-gestating ewes were observed in each batch.

Study of the Post-Infection Temperature Recordings

Figure 8:
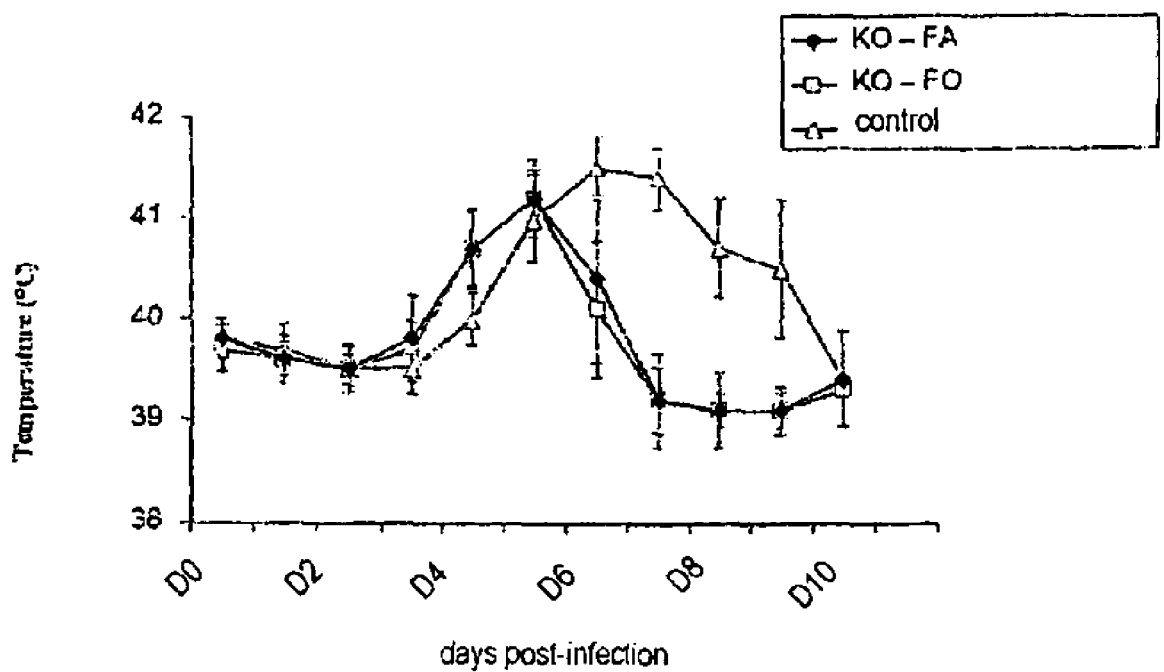

The means of the post-infection temperatures of the ewes of the various batches are represented in FIG. 8.

Following the infection, a hyperthermia is observed in all the ewes.

In the control batch, the febrile peak lasted five days from D5 to D9, with a maximum at 41.5° C. at D6. For the two immunized batches, the febrile peak lasted three days from D4 to D6, with a maximum at 41.2° C. at D5.

At the moment of the febrile peak observed for the control batch (D6), the temperatures of the ewes of the KO FA and KO FO batches have already fallen (between 40.0 and 40.5° C.), whereas the peak observed in the ewes of the control batch is maintained up to D7 and then decreases gradually up to D9, where the mean temperature observed is 40.5° C. (for KO FA and KO FO from D7 to D9: 39.0° C.).

The febrile peak of the immunized ewes is earlier, less prolonged and with a lower febrile maximum than that of the control batch.

Monitoring of Abortions and Births

At birth, the dead or viable lambs are identified and weighed.

Two types of abortion exist:
febrile abortions due to the rise in temperature following the infection with the oocysts;
infectious toxoplasmic abortions due to the development of the parasite in the fetus.

Febrile Abortions

These abortions occur subsequent to the thermal peak which follows the infection.

The results are summarized in Table I below.

TABLE I

| Batch | Control | KO FA | KO FO |
| --- | --- | --- | --- |
| Febrile abortions | 6/10 | 0/10 | 0/10 |

Six ewes of the control batch aborted within two weeks following the infection. On the other hand, no febrile abortion was observed in the immunized ewes.

Abortions Due to Infection With Toxoplasma

These abortions occur during gestation, because the parasite crosses the placenta and develops in the fetus. They are generally observed at the end of gestation.

The results are summarized in Table II below.

TABLE II

| Batch | Control | KO FA | KO FO |
| --- | --- | --- | --- |
| Infectious abortions | 4/10 | 1/10 | 3/9 |

For the interpretation of these results, one ewe of the KO FO batch was excluded: this is because, in the case of this ewe, the lambing was difficult: one of the two lambs was viable. However, it was ignored by its mother and did not survive: it was therefore not included in the results.

In the control batch, none of the four ewes which had not undergone a febrile abortion carried its gestation to term and gave birth to a viable lamb.

For the low dose batch (KO FA), only one ewe out of ten aborted.

For the high dose batch (KO FO), three abortions out of nine ewes were recorded.

The overall percentage of vaccine protection was evaluated as a function of the total number of abortions (febrile+infectious). When the ewe has had two lambs, one of which is alive, the aborted lamb is not considered in the results because several hypotheses other than infection can be envisioned in order to explain this abortion: a lack of room during gestation or a lack of interest and care for its lamb just after birth; these ewes are therefore counted as protected by the immunization.

The results are summarized in Table III below.

TABLE III

| Batch | Control | Low dose | High dose |
| --- | --- | --- | --- |
| Number of abortions | 10 | 1 | 3 |
| Total number of ewes | 10 | 10 | 9 |
| Percentage protection | 0% | 90% | 67% |

The percentage protection of the KO FA batch is 90%, versus 67% for the KO FO batch. For the control batch, the protection is zero.

Viable Lambs

Seven lambs are viable at birth for nine gestating ewes in the high dose batch, versus nine viable lambs for ten gestating ewes in the low dose batch. These lambs are in good health and do not have any malformation. The weights range from 2200 to 5200 g and correspond to normal weights for a full-term lamb (gestation period of five months).

EXAMPLE 6

Comparison of the MIC1-3KO Strain and of the S48 Strain (TOXOVAX, Schering-Plough)

Comparison of the Immunoelectrophoretic Profiles of MIC1-3KO Tachyzoites and of S48 Tachyzoites The total proteins of tachyzoites of the mic1-3KO and S48 strains were analyzed by SDS-PAGE electrophoresis under non-reducing conditions and Western blotting, as described in example 1 above. The Western blots were revealed using anti-MIC3 (T82C10) or anti-MIC1 (T101F7) monoclonal antibodies, a serum from a mouse infected orally with the *T. gondii* strain 76K, or a serum from a naïve mouse. The results are presented in FIG. 9.

Figure 9:
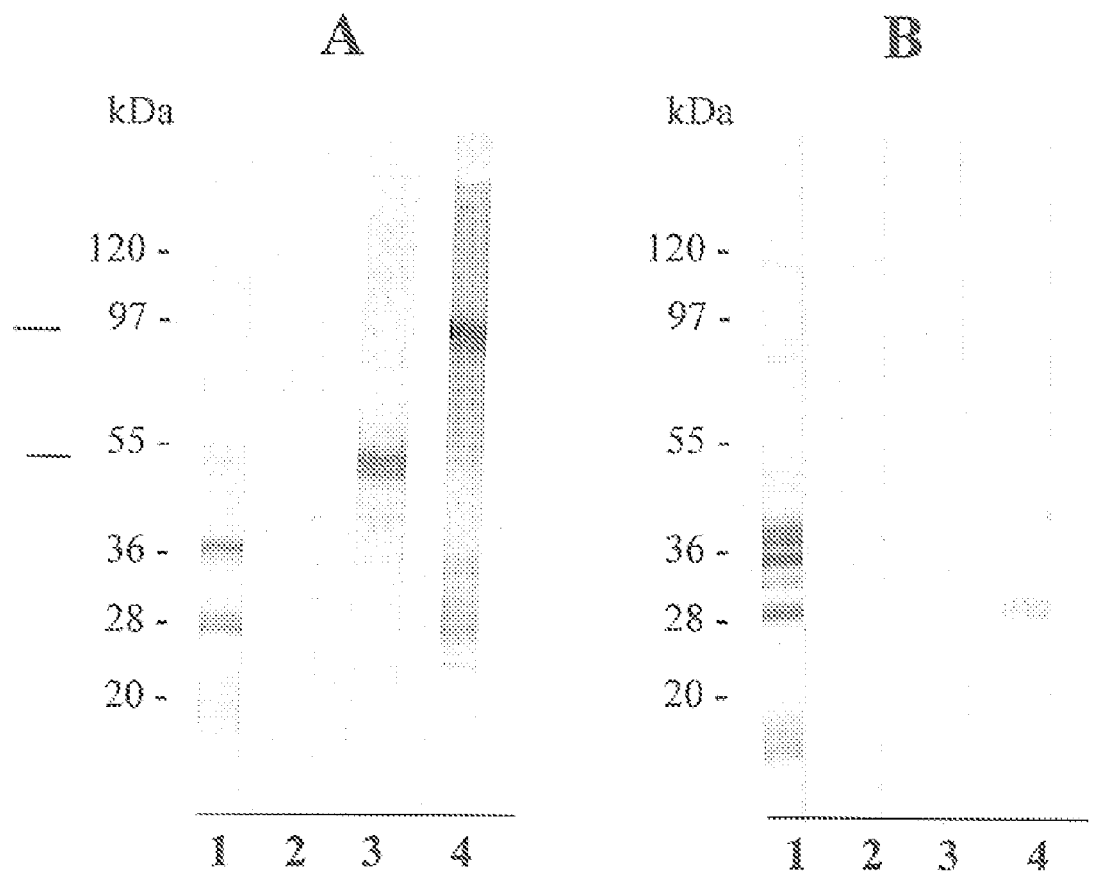

Legend to FIG. 9: (A) S48 tachyzoite lysate; (B) mic1-3KO tachyzoite lysate. Lane 1: anti-76K serum; lane 2: naïve mouse serum; lane 3: anti-MIC1; lane 4: anti-MIC3.

These results show that the mic1-3KO and S48 strains have very different electrophoretic profiles, and in particular that, unlike the mic1-3KO strain, the S48 strain expresses the two proteins MIC1 and MIC3.

Comparison of the Vaccine Protection Conferred by the mic1-3KO and S48 Strains

The vaccine protection conferred by one or other of these strains was evaluated using the protocol of example 5 above.

For this, a flock of seronegative ewes was divided up into three batches:
- a control batch of 12 ewes;
- a batch (Toxo KO 1-3) of 13 ewes, immunized with $10^5$ tachyzoites of the mic1-3KO strain;
- a batch (Toxo S48) of 12 ewes, immunized with $10^5$ tachyzoites of the S48 strain.

After inoculation with the vaccines, the following measurements were carried out on each of the batches:
- recording of the post-immunization temperatures,
- monitoring of the humoral response by the ELISA technique,
- infection of the gestating females with 400 oocysts of the PRU strain,
- recording of post-infection temperatures,
- monitoring of abortions and births.

Post-Immunization Temperatures

Figure 10:
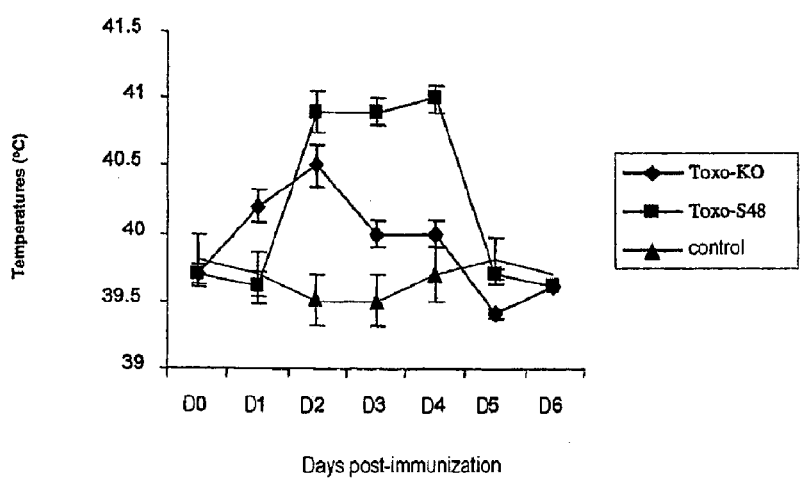

The means of the post-immunization temperatures of the ewes of the various batches are represented in FIG. 10.

Post-Immunization Humoral Response

Figure 11:
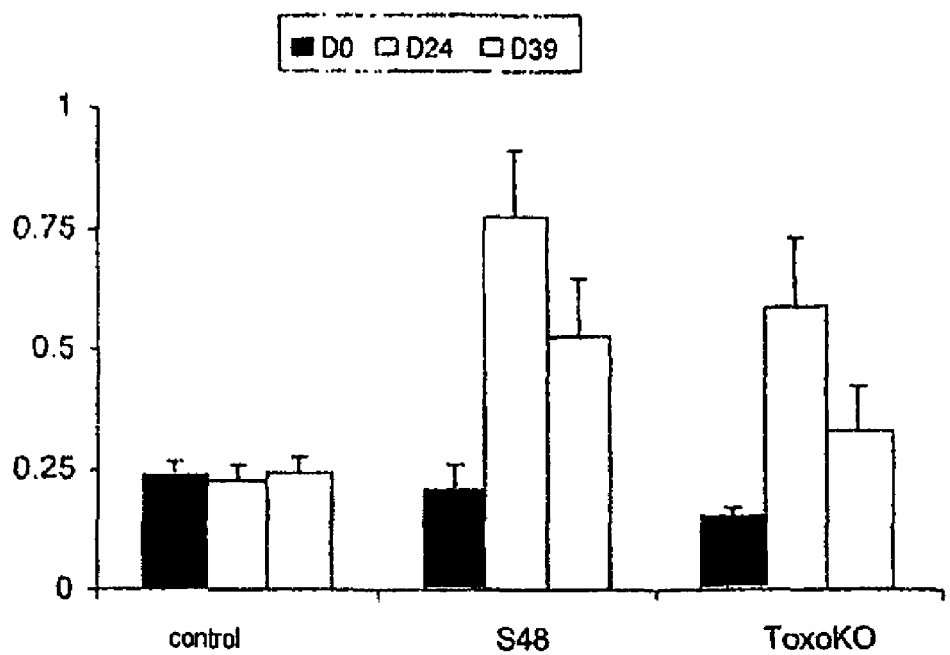

The means of the results of the ELISA assays at D0, D24 and D39, for the sera of the various batches of ewes, diluted to 1/100, are represented in FIG. 11.

Gestation Yield

After servicing by the male, 11 control ewes (out of the initial 12), 12 ToxoKO ewes (out of the initial 13) and 12 Toxo S48 ewes (out of the initial 12) were in gestation.

Post-Infection Temperatures

Figure 12:
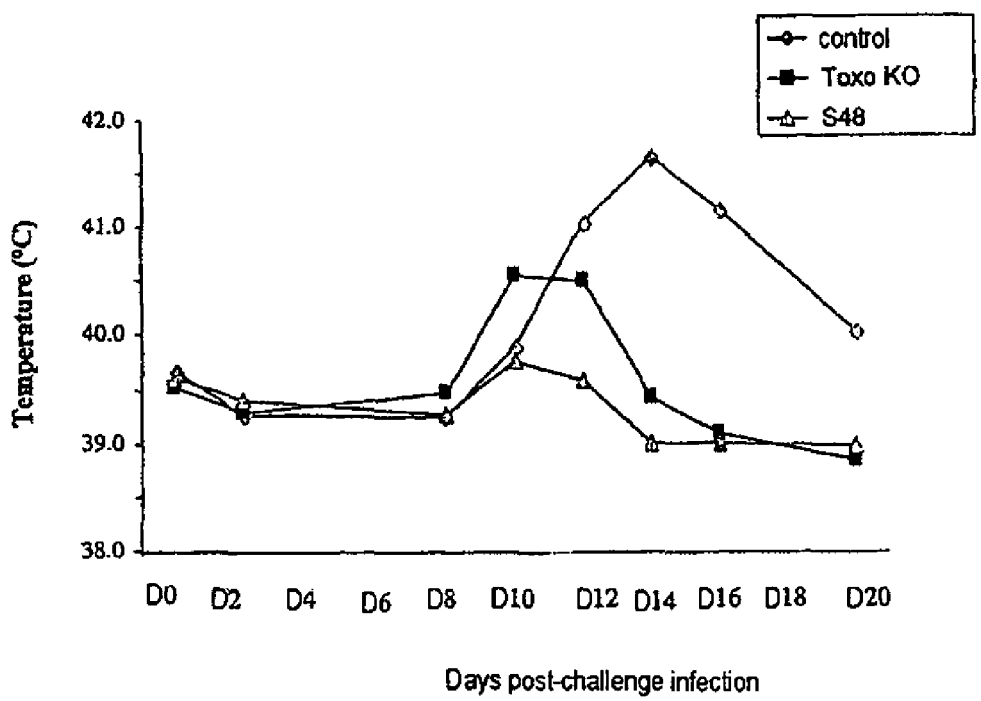

The means of the post-infection temperatures of the ewes of the various batches are represented in FIG. 12.

Monitoring of Abortions and Births

Febrile Abortions (1 Week After the Thermal Peak of the Challenge Infection)

The results are summarized in Table IV below.

TABLE IV

| Batch | Controls | ToxoKO | S48 |
|---|---|---|---|
| Febrile abortions | 10/11 | 0/12 | 0/12 |

Infectious Abortions (During the Last 2 Weeks of Gestation
The results are summarized in Table V below.

TABLE V

| Batch | Control | ToxoKO | S48 |
|---|---|---|---|
| Infectious abortions | 1/11 | 4/12 | 4/12 |

Overall Protection:
The results are summarized in Table VI below.

TABLE VI

| Batch | Control | ToxoKO | S48 |
|---|---|---|---|
| Number of abortions | 11 | 4 | 4 |
| Total number of gestating ewes | 10 | 12 | 12 |
| Percentage protection | 0% | 66.6% | 66.6% |

The percentage protection is 66.6% for each of the ToxoKO and ToxoS48 batches. For the control batch, the protection is zero.

The 2 strains MIC1-3KO and S48 therefore confer a similar level of protection.

---

The invention claimed is:

1. A mutant strain of *Toxoplasma gondii*, in which adhesin MIC1 and adhesin MIC3 are inactivated by deletion of each of MIC1 and MIC3 genes.

2. A composition comprising the mutant strain of *Toxoplasma gondii* as claimed in claim 1.